United States Patent [19]

Cadieux et al.

[11] Patent Number: 4,676,871

[45] Date of Patent: Jun. 30, 1987

[54] AIR LAID PEAT MOSS BOARD

[75] Inventors: Serge M. Cadieux, Pierre Fonds; Martin Lemay, Montreal, both of Canada

[73] Assignee: Johnson & Johnson, New Brunswick, N.J.

[21] Appl. No.: 770,549

[22] Filed: Aug. 29, 1985

[51] Int. Cl.$^4$ ............................................. D21B 1/06
[52] U.S. Cl. ........................................ 162/13; 162/92; 162/150; 162/205; 162/206; 264/115; 264/116; 264/121; 264/175; 264/517; 264/518
[58] Field of Search ................. 162/92, 148, 150, 205, 162/206, 13; 37/3; 264/115, 116, 121, 175, 517, 518; 156/62.2

[56] References Cited

U.S. PATENT DOCUMENTS

| 4,215,692 | 8/1980 | Levesque | 162/92 |
| 4,473,440 | 9/1984 | Ovans | 162/148 |

FOREIGN PATENT DOCUMENTS

| 1804 | of 1853 | United Kingdom | 162/92 |
| 3297 | of 1881 | United Kingdom | 162/92 |
| 2129844 | 5/1984 | United Kingdom | 162/92 |

Primary Examiner—Peter Chin
Attorney, Agent, or Firm—Jason Lipow

[57] ABSTRACT

Dry laid board comprising peat moss is provided and made by harvesting peat moss having a degree of decomposition of H-1 value as measured by the Modified Von Post Scale, individualizing the harvested peat moss, drying the individualized peat moss and entraining the peat moss in a gas stream. The entrained peat moss is then condensed to form a low density peat moss containing board which is subsequently calendered for use in such products as dressings, diapers and sanitary napkins.

14 Claims, 3 Drawing Figures

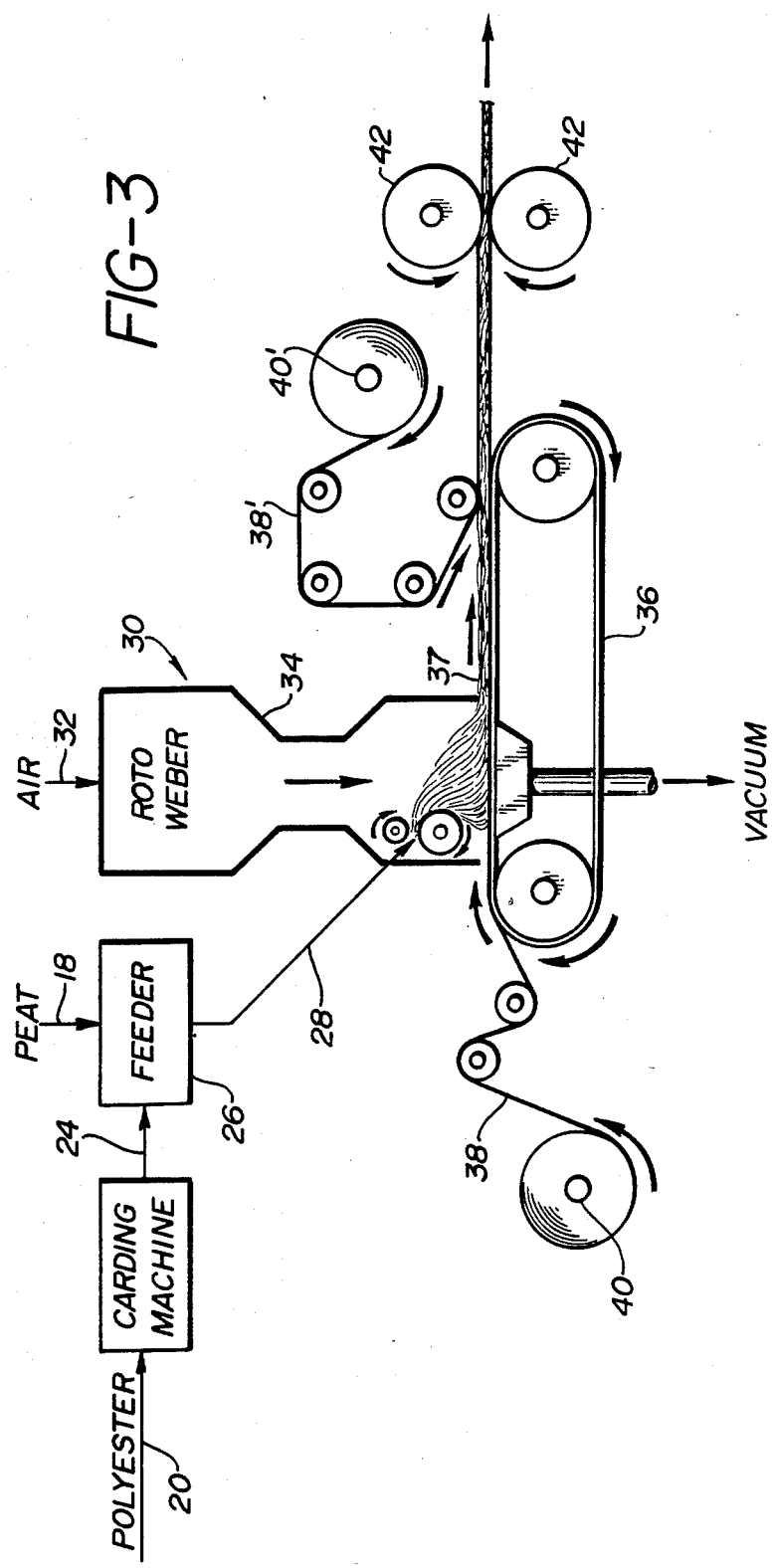

AIR LAID PEAT MOSS BOARD

BACKGROUND OF THE INVENTION

This invention relates to a process for economically producing absorbent board from peat moss and more particularly to a process for air laying peat moss to form an absorbent, flexible, strong board capable for use in such diverse products as body fluid absorbent products, e.g., sanitary napkins, dressings, diapers and the like, as well as in horticultural products, e.g., as a mulch for growing plants.

The use of peat moss, in combination with other fibrous materials, for absorbent products, has been suggested in several prior disclosures such as for example, U.S. Pat. Nos. 4,170,515; 4,226,237; 4,215,692; and 4,507,122. Additionally, processes have been suggested for incorporating peat moss into a fibrous board product, such processes exemplified by U.S. Pat. Nos. 751,139 and 4,473,440.

The latter cited U.S. Pat. No. 4,473,440 is particularly pertinent as it discloses a process for producing aborbent, flexible peat moss board for use in absorbent products. In accordance with the teachings of this patent, sphagnum peat moss is first screened to remove large materials such as roots and branches and to remove fine particles, i.e., those passing through a 100 mesh screen. The screened peat moss, optionally combined with other fibrous material, is then formed into an aqueous slurry having a solid content of from 0.1 to 1.0% by weight. The slurry is then flowed onto a Fourdrinier wire where it is dewatered to form a low density board. The board is dried to a critical moisture content and then calendered to provide a highly absorbent flexible peat moss containing board.

While, in the main, the product resulting from this prior art process is quite satisfactory for use in absorbent products, by following the teachings of this process certain drawbacks are encountered.

Firstly, the requirement of providing screened peat moss creates great economic burdens to the process. Because both large and small particles of harvested peat moss are discarded in the course of the screening, essentially only half the material handled during harvesting and screening is actually utilized in the product. Yet this fact notwithstanding, the process cannot tolerate large particles without grinding and certainly cannot tolerate small particles, i.e. peat moss fines, in that the Fourdrinier wire would quickly become blocked by such fine particles and soon render further efficient wet laying of board impossible. Thus, the efficiency, as measured by raw material usage, is poor.

Further, the wet laid process of the prior art requires that the board be laid from a very dilute slurry, dewatered on the Fourdrinier wire and then dried to the prescribed moisture level prior to calendering to produce the flexible absorbent board. As is evident, it is necessary therefore, to accomplish the drying of the peat moss at a point in the process after the board is formed, i.e., at a point in the process whereat drying is most difficult, entailing expensive drying equipment and great energy input.

Still further, because of the inherent limitations in a wet laid process, the choice of other fibrous materials to be combined with the peat moss is necessarily limited. Too fine particle sizes cannot be tolerated and other fibers, having relatively long length, become entangled in clumps and destroy the uniformity of the resulting product.

Accordingly, there is a need for an improved process for producing flexible, absorbent peat moss board.

SUMMARY OF THE INVENTION

In accordance with the teachings of this invention, a process is provided for producing absorbent flexible peat moss board which overcomes the drawbacks associated with prior suggestions, i.e., makes greater use of the harvested peat moss, greatly facilitates the drying process and increases the choice of other materials which may be incorporated, along with the peat moss, in the finished board.

Specifically, the process of this invention comprises the steps of harvesting primarily that peat moss having a degree of decomposition of H-1 value as measured by the Modified Von Post Scale with no more than thirty-three percent of said harvested peat moss having a degree of decomposition of H-2 value or more. The harvested peat moss is then individualized and dried, preferably by pneumatic conveying drying means. The dried individualized peat moss particles are then air laid by dispersing the particles in a high velocity air stream and condensing (i.e. depositing) the particles onto a foraminous substrate such as a perforated cylinder or wire screen or belt to produce the low density board. The board is then calendered to produce the flexible absorbent product of this invention.

In carrying out this process, the drying step is carefully controlled to insure that the moisture content in the board presented to the calendering step is within the limits required to produce satisfactory product. Such limits are set out in the aforementioned U.S. Pat. No. 4,473,440 which is incorporated herein by reference.

Surprisingly, when employing the wet laying process of the prior art, the harvesting technique with respect to the degree of decomposition is a relatively unimportant factor in producing a board of desirable absorbency. On the other hand, when employing the dry laying process of this invention, such selection at harvesting is of prime importance and board made from relatively undecomposed peat moss results in highly absorbent product whereas a board made from relatively decomposed peat moss is substantially less absorbent.

In a preferred embodiment, long, thin fibers are added to the particulate peat moss to enhance the strength of the resulting board. Again, it is only by utilizing the process of this invention that such addition is possible without the clumping and knotting problems associated with the prior art wet laid processes.

Brief Description of the Drawings

FIG. 3 is a schematic flow sheet of the air laying and calendering steps of the process of this invention.

DETAILED DESCRIPTION OF THE INVENTION

Figure 1:
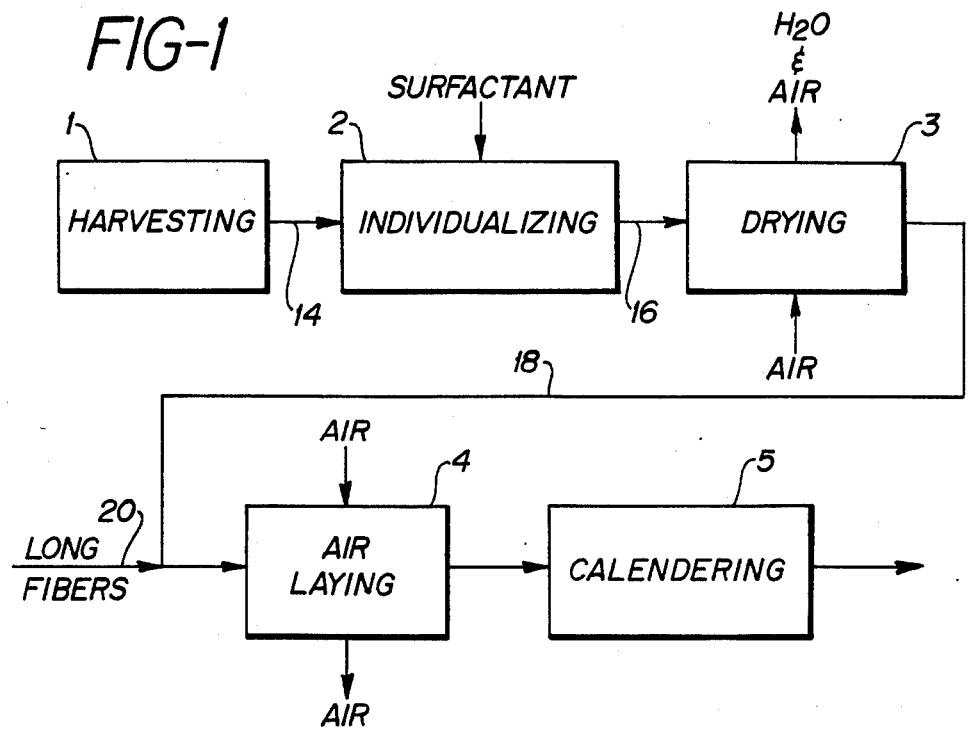
FIG. 1 is a schematic flow sheet illustrating the various steps of the process of this invention.

Referring now to FIG. 1, illustrated therein, in schematic view, is a process flow sheet illustrating the steps of this invention which include harvesting 1, individualizing 2, drying 3, air laying 4 and calendering 5.

Figure 2:
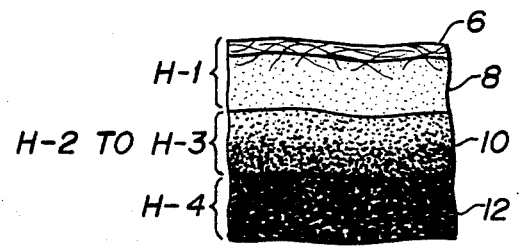
FIG. 2 is a schematic cross-sectional view of a typical peat bog.

As has been described, the peat moss usable for the dry laying process of this invention is selected by harvesting only essentially undecomposed peat moss having a Modified Von Post Value of H-1 and in no event including more than thirty-three percent (by weight, based on dry peat moss) of peat moss having a degree of degradation greater than H-2 or more. The Modified Von Post method of characterizing the degree of decomposition of a stratum of peat moss is the art accepted field test and is described in detail in "Peat Bogs of the Inhabited Part of Roberval, Lac St. Jean, Dubuc and Chicoutini Counties"; a publication of the Ministére Des Richesses Naturelles Du Québec, Director Générale Des Mines; authored by Antoine Simard, Québec 1974. As is well known, peat bogs typically have a vertical cross-sectional stratification as is illustrated in FIG. 2. The top most layer 6 is comprised of the leaves, branches and flowers of living plants, predominately the living peat moss plant but also includes other plants growing on the bog. Such top-most layer extends typically from the surface to a depth of from about 1.0 inch to 6.0 inches. Below this layer is a layer 8 of undecomposed peat moss which comprises leaves, branches and flowers of dead peat moss as well as the roots of living plants. This layer is characterized by being fibrous, relatively light colored, with the plant structure generally intact. Such a layer 8 typically is from at a depth of from 1.0 to 3.0 ft. below the surface. Below layer 8 is a layer 10 of partially decomposed peat moss which generally can be distinguished from layer 8 by a clear line of color demarcation, layer 10 being considerably darker than layer 8. Layer 10 is characterized by increasingly darkening color and increasing degradation of the plant structure with increasing depth to a point where the plant structure is no longer apparent and the material shades from brown to black. The lower portion of this layer 10 is typically the portion of a peat bog utilized as fuel. This layer 10 typically extends from a depth of about 3 ft. to about 8 ft. from the surface.

Below layer 10 is layer 12 which is the last stage of decomposition of the peat moss. This layer 12 is generally referred to as "black earth" and is characterized by having essentially no plant structure and a black color. This material is generally found at a depth of from about 8 ft. to about 12 ft. from the surface. In some instances, bogs do not contain such a layer.

The Modified Von Post Scale assigns values to each stratum of from H-1 to H-4 with increasing degree of decomposition. The test consists of pressing samples of each peat stratum and examining the expelled water. An H-1 value is assigned to an undecomposed fibrous peat stratum which, when pressed, expells a clear liquid. An H-2 value is assigned to a partially decomposed stratum, having some plant structure, which, when pressed, expells a dirty liquid but one which is free of organic particles. An H-3 value is assigned to highly decomposed peat of the fuel type which, when pressed, expells a muddy water mixed with brown and black organic matter. Finally, an H-4 value is assigned to the so-called "flowing" sedimentary peats, known as black earth, which when pressed in the hand ejects all of the sample material through the fingers.

The objective of the harvesting step of this invention is to extract from the bog essentially only the H-1 value peat moss and this may be accomplished by selecting the layer 6 and 8 and excluding the layer 10. As discussed above, there is generally a line of demarcation, based on color change, between layers 8 and 10 that is visible to the eye and can be relied upon to insure that predominately H-1 material is being harvested. Inevitably however, some H-2 or higher degree of decomposition material may be included. It has been discovered that about no more than thirty-three percent H-2 or higher material may be employed in the process of this invention. Preferably no more than 10.0% is employed. As will be seen from the description herein, the properties of the resulting dry laid board are greatly compromised by the inclusion of greater quantities of decomposed peat, whereas such was not noted when employing a prior art wet laid process. To date we have no explanation for this phenomenon.

The method of choice for harvesting the selected peat moss from the bog is the so-called Haku method developed in Finland and modified so that the selection of essentially undecomposed peat moss may be accomplished in accordance with the teachings of this invention. A series of trenches are dug into the area of the bog being harvested, draining into main trenches. After trenching and allowing some time for drainage, the bog is profiled, i.e., surface material is moved from between two adjacent trenches toward the centerline between these trenches. This may be accomplished, for example, by use of a large screw machine pulled by a tractor. After profiling, the bog is milled, i.e., the surface is fluffed to facilitate removal for usable material. A ridger is then employed to scrape off approximately two inches of the top most layer which is then loaded and stored or immediately used in the further process steps of this invention. The milling and ridging steps are then repeated with the removal of successive two inch layers until all of the desirable material has been removed from the harvested area of the bog.

The harvested peat 14, consisting of material ranging in sizes of from 1/16 inch to 4 inches in its largest dimension contains water in an amount of from about 70.0 to about 80.0% by weight, based on the wet peat. This material is then passed to an individualizing step 2 wherein the harvested peat stream 14 is treated to breakup large clumps and pieces. Perferably, a surfactant material is added at this point in the process to enhance the wetting characteristics of the finished board. Such surfactant may be showered onto the raw harvested peat moss stream 14 by employing a dilute water solution, e.g. 0.1% by weight of surfactant. A particularly useful surfactant is a sodium dioctyl sulfosuccinate containing agent manufactured by the Rohm & Haas Company and sold by them under the trademark Triton GR-5.

The showered harvested peat may be individualized in any of a variety of available equipment known in the art. Of choice, the harvested peat is fed to a hammer mill which, in addition to performing the functions of breaking up clumps and large pieces also aids in homogenizing the addition of surfactant.

As a result of the showering process, the harvested showered peat will increase in water content, e.g., to about 85 to 90% water by weight, and hence is preferably passed to a wet press where water is removed down to a level of about 60 to 75% by weight. A particularly useful wet press is of the type maunfactured by Kamyr Inc. of Glens Falls, N.Y. under the trademark KAMYR RING PRESS wherein a rotating screen ring forms a circumferential channel with the walls of the press. Entering wet peat concentrates in the front end of the rotating ring. The friction of the turning ring against the concentration of entering wet peat causes the peat to becomes progressively dewatered and pressed toward the outlet of the device. Compaction of the exiting material is promoted by a restriction plate at the press outlet which can be adjusted to increase or reduce the outlet opening size. Such a device is particularly useful in that, in addition to dewatering, large fibrous particles, e.g., roots are defibrilated. Further, the surfactant is further distributed. The wet pressing step is advantageously followed by a second stage of individualizing by utilizing a second hammer mill wherein further debrilation takes place and the wet press effluent is fluffed for processing in the drying step 3.

The fluffed individualized peat moss stream 16 is passed to the drying step 3. Drying of this particulate material may be accomplished by any of several methods well known in the art and capable of reaching the required level of dryness without destroying the structure and absorbent properties of the peat moss. In this connection, the peat moss must be dried to a moisture content such that peat moss delivered from the air laying step 4 to the calendering step 5 has the requisite moisture content as has already been suggested in the aforementioned U.S. Pat. No. 4,473,440. This moisture content is a function of the peat moss concentration in the finished board but can be stated generally to vary between about 5 to about 35% water, based on the weight of the wet board. It will be appreciated that to achieve this moisture content at the entrance point to the calendering step 5, it is necessary to control the moisture content leaving the drying step 3, to a higher valve in that appreciable moisture is lost from the peat moss in the intervening steps between drying and calendering. Accordingly, in order to achieve the prescribed moisture levels of between 5 and 35% at calendering, it is necessary to control moisture levels exiting the drying steps to between 6 and 45%.

Drying processes useful herein generally involve elevating the temperature of the peat moss in order to drive off the water. The maximum temperature to which the peat moss is elevated in the course of drying is a function of several factors. A high temperature is, of course, most effective for rapidly removing water and may require a lower residence time in the equipment and hence smaller and cheaper equipment. Additionally, a high temperature is useful to insure that micoorganisms present in the harvested peat moss are destroyed and this is important when employing the finished board in products used for medical or personal hygiene purposes. On the other hand high temperature drying may be less efficient from a utilities requirements point of view and moreover, it has been noted that when peat moss is subjected to high temperatures the surface characteristics of the peat moss change so as to impair absorptive properties such as retention and rate of absorption of liquids. This impairment due to drying may be compensated for by adding surfactant to the product as is suggested at the individualizing step 2. Accordingly, it can be seen that optimum drying temperatures is an economic balance among various factors, one of which being the ultimate use of the finished product. In any event, however, the maximum drying temperature in the drying step should not vary outside the range of from about 100° C. to about 300° C., with a suitable temperature being about 150° C. for most applications.

Among the usable drying processes are those employing rotary dryers, steam dryers, and, generically, pneumatic conveying dryers including flash dryers such as the Raymond flash dryer or the Vertex or spin flash dryer. Pneumatic conveying dryers are of the type wherein the material to be dried dispersed in a hot gas zone followed by conveying at high velocities. The dryer is essentially a device for dispersing a wet solid in a hot gas, e.g., including a duct through which the gas conveys the dispersed particles and collection system, usually a cyclone separator, for collecting the dried solids. Preferably, to best achieve the drying levels required in the process of this invention, two flash dryers are used in series. It will be appreciated that this drying technique is highly efficient primarily because of the highly dispersed condition of the peat moss to be dried. It should be noted that such a technique is not applicable to the prior art wet laying processes in that, of necessity, it is an already formed board that must be dried in accordance with these prior processes and hence a dispersing gas system cannot be used.

The dried peat moss stream 18 may now be passed onto the air laying step 4 or alternatively may be stored for future use. If stored, preferably the peat moss is baled and protected from moisture pick up or loss while in storage.

In the air laying step 4 of this invention, the dried peat moss is optionally combined with other materials, e.g., long fibers for strength, and air laid into a low density board. FIG. 3 illustrates in greater schematic detail an air laying process wherein the dried peat moss stream 18 is combined with polyester fibers 20. Polyester fibers are advantageously added to the peat moss to impart additional strength to the resulting board. Since these fibers are not hydrophilic, to a degree, their inclusion detracts from the absorbent properties of the resulting board and hence it is desirable to strike a balance between strength and absorbency in choosing the quantity, length and thickness of these fibers. It has been discovered that, advantageously, a quantity of such fibers amounting to about 1 to about 15% by weight, based on the total weight of the finished bone dry board may be employed. The fibers should have as low a denier and as long a length as can be tolerated by the processing equipment and specifically may vary in length from about ⅜ to about 2 inches with a denier of about one to six. While such fibers are exemplified by polyester, other long, strong, fibers are usable provided they fulfill the function of strength without undue impairment of absorptive properties. For example, fibers of glass, polypropylene, nylon, polyacetate and rayon may all be used.

Referring again to FIG. 3, the exemplified polyester fibers 20 are fed to a carding machine 22 wherein they are separated and formed into a light carded web 24. The web 24 is combined with the dried peat moss 18 in volumetric feeder 26 wherein the peat moss is laid down upon the web in a predetermined uniform thickness which insures the desired ratio of peat moss to polyester. Such volumetric feeders are already available, one such device being sold by the Curt Joa Company. The peat moss and polyester effluent 28 of the volumetric feeder 26 is then fed to the air laying board former 30. The board former usable in the process of this invention may be any of a variety of air laying web formers already suggested for use in processes for air laying nonwoven webs. Generally, these formers must be capable of dispersing the polyester and peat moss web 28 in a high velocity gas stream, advantageously air, and condensing, i.e., depositing the particles onto a foraminous substrate such as a perforated cylinder or wire screen or belt to produce the low density board. Examples of such formers which may be adapted for use in the process of this invention are disclosed in U.S. Pat. Nos. 3,768,118; 3,740,797; and 3,772,739. For example, an air stream 32, preferably induced by a blower, is introduced into the former and controlled to a high velocity by passing through a restricted cross-sectional flow area 34. The web 28 is passed to the inlet of one or more rotating lickerins which individualize the peat moss and polyester particles and deliver them for entrainment by the high velocity air stream. The solids in the air stream are condensed on a foraminous moving endless belt 36 in the form of a wire thereby laying down a low density, generally uniformly thick, board 37. Condensation is enhanced by imposing a vacuum on the side of the belt opposite to where the board is being formed.

Operating conditions for the former such as quantity and velocity of the air stream, lickerin speeds, degree of vacuum, speed of the wire and the like are all dependent on such factors as the specific equipment employed, the desired uniformly of the resulting board, the desired base weight of the board, among others. Air quantities, for example, may vary from 10 ft.$^3$ per lb. of solids to 300 ft$^3$ /lb.; lickerin speeds may vary from 500 to 1500 rpm; line speeds may vary from about 5.0 meters/min to about 100.0 meter/min; and vacuum levels may vary from about 30 to about 80 inches of water.

It will be understood that while the process exemplified utilizes the volumetric feeder as the means for mixing the long fibers with thee peat for board forming in the former, other methods are equally usable. For example, the peat alone may be fed via a volumetric feeder to one rotor of a dual rotor webber such as is described in the above-cited patents. The polyester may separately be fed to the other rotor and the two materials may be mixed within the board former itself.

In a preferred embodiment of this invention, it is desirable to provide the finished board with a lamination on one or both faces which serve to reduce any dusting of peat moss in use or in handling the board and to mask the generally nonwhite color of the peat board as is desired in certain medical and personal hygiene uses. Such laminations may comprise bleached wood pulp fibers, e.g., kraft wood pulp which may, for example, be air laid onto the wire either before or after the air laying of the peat moss to produce a laminate on either of the board faces. Of course, such wood pulp may be air laid both before and after the air laying of the peat moss to produce laminations on both faces. In a preferred embodiment, the wood pulp is supplied to the board in the form of a previously formed web, e.g., a tissue. As is illustrated in FIG. 3, tissue 38 is provided from unwind stand 40 to the wire 36 upstream of the peat laying position. Additionally, tissue 38' is provided from unwind stand 40' to board 37 downstream of the peat moss laying position. Accordingly, tissue is laminated to both faces of the board. Lamination of tissue may be aided by first spraying the tissue with water and hence spray heads (not shown) may be provided at appropriate positions in the process. The tissue choosen will, of course, depend on the desired final use of the board. For use in medical or personal hygiene products it has been discovered to be advantageous to employ tissue having a basis weight of from about 10 to about 30 gm/m$^2$.

The board 37 leaving the air laying step 4 (FIG. 1) is then passed to the calendering step 5. Board 37 may have a density ranging from about 0.01 to about 0.09 gm/cc. in accordance with the teachings of this invention, the board has been carefully conditioned so as to contain the moisture content prescribed by the teachings of U.S. Pat. No. 4,473,440. This has been accomplished by controlling the drying step 3. This moisture content will generally vary between about 10 to about 25% by weight, water. The board 37 is then passed between calender rollers 42 to produce the densified flexible absorbent board of this invention. The rollers are set so as to produce a board densified to the desired degree of compression. For most purposes a highly flexible absorbent board results when compressed to a density of from about 0.4 to about 1 gram/cc. Such compression may be accomplished from rollers exerting a compression force of from about 1000 to about 10,000 pounds per linear inch.

To better illustrate the teachings of this invention, the following examples are given.

EXAMPLE 1

Peat moss is harvested from a bog by utilizing the above-described Haku method. The peat moss is taken from the stratum lying between the surface of the bog down to a depth of 2.5 feet and, as tested by the Von Post method, has a Von Post value of H-1. The harvested peat moss has a moisture content of 70% water, by weight, based on wet peat moss.

The peat passes under a shower of a dilute solution of Triton GR-5 surfactant, present in sufficient quantity to deposit 0.6% by weight of surfactant based on the weight of peat.

The peat moss is next passed to a hammer mill wherein large fibrous particles are broken up and defibrilated and the surfactant is intimately combined with the peat moss. The material leaving the hammer mill, having a water content of between 85% and 90% by weight, based on the weight of the wet peat, is next passed to a wet press wherein the moisture level is reduced to about 65% and further homogenizing and defibrilating occurs. Effluent from the wet press is passed to a second hammer mill wherein further individualizing occurs in preparation for introduction into a series of two flash dryers.

The effluent of the second hammer mill is dried, in two stages of flash drying utilizing air having an inlet temperature of 150° C. and drying the peat moss to a level of about 35% water, by weight, based on wet peat moss. The dried peat moss is compressed to about 0.3 gm/cc and baled in polyethylene protective packaging and stored for further processing.

Baled material obtained from storage is further processed by being combined with polyester fibers having a length of 1⅜ inches and a denier of 1.5. The polyester is carded into a light web, 15 gm/m$^2$ basis weight, and then combined with debaled peat moss in a volumetric feeder so as to maintain a quantity of 2.0% by weight of polyester, based on the combined weight of peat moss and polyester.

The effluent of the volumetric feeder is feed to a board former of the type described in U.S. Pat. No. 3,768,118. Lickering speeds are operated at 800 rpm and the individualized polyester fiber peat moss mixture is entrained in an air stream utilizing about 230 ft$_3$ of air per lb. of solids. The solids are condensed on a endless wire belt upon which a layer of tissue, having a basis weight of 15 gm/m$^2$, if first provided. The belt travels at a speed of 30.0 m/min and a board is laid thereon having a basis weight of about 300 gm/m$^2$. A second laminate of the same tissue is applied to the top most face. The resulting board leaving the board former has a density of about 0.048 gm/cc and a moisture content of 20% by weight of water based on the weight of the board.

The board is next passed through the nip of calender rolls which exert a pressure of 7,000 lbs/linear inch and is thereby compressed to a density of 0.7 gm/cc.

The board is tested for absorbency using the plate test. This test comprises placing a 4 inch by 4 inch weighed sample of board between two plates one of which is provided with an ⅛ inch diameter orifice. A weight is placed on the topmost plate to produce a pressure of 5 pounds pre square inch. Water is introduced through the orifice to saturate the board. This is accomplished by allowing the water to run continuously for at least five minutes. The volume of water retained by the board is measured and reported in units of cubic centimeters of water per gram of board. The sample board had an absorbency of 10.7 cc/gm.

COMPARATIVE EXAMPLE

A series of boards were attempted to be made employing the procedure of Example 1 with the exception that the peat harvested had approximately 40% H-2 value peat therein and was taken from the bog at a level of from 0 to 3.5 feet. The dry peat was then screened to pass through a 10 mesh screen and remain on a 40 mesh screen. Boards were made with this screened, 40% H-2 value peat moss and tested for absorbency in accordance with the procedure of Example 1. The absorbency of these boards varied from 4.5 to 7.5 cc/gm as compared to the value of 10.7 obtained when operating in accordance with the teachings of this invention. The resulting board was also darker in color and had less physical integrity.

EXAMPLE 2

A series of boards were made by employing the procedure of Example 1 with the exception that the boards contained varying amounts of H-2 value peat moss. The boards were tested for absorbency with the results set out in Table 1 below.

TABLE 1

| Sample | H-2 Peat (weight %) | Absorbency (cc/gm) |
|---|---|---|
| 1 | 0 | 9.9 |
| 2 | 33 | 6.9 |
| 3 | 66 | 5.8 |
| 4 | 100 | 4.1 |

As can be seen, when the peat moss contained a level of H-2, greater than about 33%, the absorbency of the resulting board substantially declined.

EXAMPLE 3

This example illustrates the surprising discovery that the H-2 value peat moss content is important in the dry laid process of this invention but not important in the wet laid processes of the prior art. A series of boards were prepared utilizing 100% H-1 peat moss and 60% H-1, 40% H-2 peat moss. The boards were made by both the dry laying process of Example 1 and also by the wet process as is set out in U.S. Pat. No. 4,473,440. The boards are tested for absorbency using the method of Example 1. The results are set forth in Table 2 below.

TABLE 2

| Sample | H-2 Peat (weight %) | Laying Process | Absorption (cc/gm) |
|---|---|---|---|
| 1 | 0 | Dry | 10.7 |
| 2 | 40 | Dry | 4.5–6.7 |
| 3 | 0 | Wet | 11.0 |
| 4 | 40 | Wet | 11.0 |

As can be seen the quantity of H-2 peat moss has a significant effect on absorbency for the dry process of this invention and essentially no effect in the wet laying process of the prior art.

What is claimed is:

1. A process for producing absorbent board from peat moss comprising:
   (a) harvesting peat moss having a degree of decomposition of H-1 value as measured by the Modified Von Post scale with no more than 33% by weight of said harvested peat moss having a degree of decomposition of H-2 value or more;
   (b) individualizing said harvested peat moss;
   (c) drying said individualized peat moss;
   (d) entraining said dried peat moss to form a low density board;
   said process being carried out without separating peat moss fines from the peat moss at any point in the process.

2. The process of claim 1 wherein no more than 10% by weight of said harvested peat moss has a degree of decomposition of H-2 value or more.

3. The process of claim 1 wherein said board has a density of from about 0.01 to about 0.09 gm/cc.

4. The process of claim 1 wherein said low density board is calendered to a density of from about 0.4 to about 1 gm/cc.

5. The process of claim 4 wherein said calendering is accomplished by compression force of 1000 to about 10,000 pounds per linier inch.

6. The process of claim 4 wherein said low density board is maintained at a moisture content of from about 5 to about 35 percent by weight of moisture prior to calendering.

7. The process of claim 6 wherein said moisture content is maintained by controlling the moisture content of the dried peat moss.

8. The process of claim 1 wherein said peat moss is combined with long fibers prior to forming said low density board.

9. The process of claim 8 wherein said long fibers have a length of about ⅜ to about 2 inches and a denier of about one to six.

10. The process of claim 9 wherein said long fibers are selected from the group comprising polyester, glass, polypropylene, nylon, polyacetate and rayon fibers.

11. An absorbent flexible board comprising essentially harvested peat moss having a degree of decomposition of H-1 value on the modified Von Post scaled and no more than 33% by weight of harvested peat moss having a degree of composition of H-2 value or more; said board being made by the process of claim 1.

12. The board of claim 11 having a density of from 0.01 to about 0.09 gm/cc.

13. The board of claim 12 having been compressed to a density of from about 0.4 to about 1 gm/cc.

14. The board of claim 11 also comprising from about 1 to about 13% by weight of long fibers having a length of from about ⅜ to about 2 inches and a denier of about one to about six.

* * * * *